(12) United States Patent
Zucchetti et al.

(10) Patent No.: US 6,967,217 B1
(45) Date of Patent: Nov. 22, 2005

(54) PROCESS AND COMPOSITION FOR ENHANCING THE ACTION OF VITAMIN A ON THE CELLULAR ACTIVITY OF AN INDIVIDUAL, AND USE OF VITAMIN C

(75) Inventors: Roberto Alcantara Martins Zucchetti, São Paulo (BR); Simoni Chitarra Souza, São Paulo (BR); Luciana Villa Nova Silva, São Paulo (BR)

(73) Assignee: Natura Cosmetico S.A., Sao Paulo (BR)

( * ) Notice: Subject to any disclaimer, the term of this patent is extended or adjusted under 35 U.S.C. 154(b) by 0 days.

(21) Appl. No.: 09/786,057

(22) PCT Filed: Sep. 3, 1999

(86) PCT No.: PCT/BR99/00072

§ 371 (c)(1),
(2), (4) Date: Jun. 26, 2001

(87) PCT Pub. No.: WO00/13659

PCT Pub. Date: Mar. 16, 2000

(30) Foreign Application Priority Data

Sep. 8, 1998 (BR) ..................... 9803936

(51) Int. Cl.⁷ ..................... A61K 31/355; A61K 31/34; A61K 31/07; A61K 7/42; A61K 35/80
(52) U.S. Cl. ..................... 514/458; 514/474; 514/725; 424/59; 424/195.17; 424/489
(58) Field of Search ................ 424/401, 450, 424/455, 463, 489, 490, 451, 195.17, 59; 514/458, 474, 725, 904, 751, 844, 947, 963

(56) References Cited

U.S. PATENT DOCUMENTS

| | | | |
|---|---|---|---|
| 4,704,280 A | 11/1987 | Bates | 424/195.1 |
| 5,034,228 A | 7/1991 | Meybeck et al. | 424/401 |
| 5,230,836 A | 7/1993 | Todd, Jr. | 252/407 |
| 5,290,481 A | 3/1994 | Todd, Jr. | 252/407 |
| 5,296,249 A | 3/1994 | Todd, Jr. | 426/541 |
| 5,314,686 A | 5/1994 | Todd, Jr. | 424/401 |
| 5,395,620 A * | 3/1995 | Huc et al. | 424/489 |
| 5,851,538 A | 12/1998 | Froix et al. | 424/401 |
| 5,891,470 A | 4/1999 | Rinaldi et al. | 424/451 |
| 6,015,548 A | 1/2000 | Siddiqui et al. | 424/59 |
| 6,228,894 B1 * | 5/2001 | Rinaldi et al. | 514/951 |

FOREIGN PATENT DOCUMENTS

| | | |
|---|---|---|
| EP | 0 229 561 | 7/1987 |
| EP | 0 781 551 | 7/1997 |
| FR | 2 612 775 | 9/1988 |
| JP | 62000013 | 1/1987 |
| WO | WO 9300015 | 1/1993 |
| WO | WO 94/09756 | 5/1994 |
| WO | WO 99/24011 | 5/1999 |
| WO | WO 99/33439 | 7/1999 |

* cited by examiner

*Primary Examiner*—Raymond J. Henley, III
(74) *Attorney, Agent, or Firm*—Smith, Gambrell & Russell

(57) ABSTRACT

The present invention refers to a process, a composition and the use of Vitamin C for enhancing the action of Vitamin A on the cellular activity of an individual. According to the invention, the association of Vitamin C to Vitamin A will be applied to said individual at a weight ratio ranging from 1:1 to about 10:1.

16 Claims, 1 Drawing Sheet

FIG. 1 - With exposure to radiation
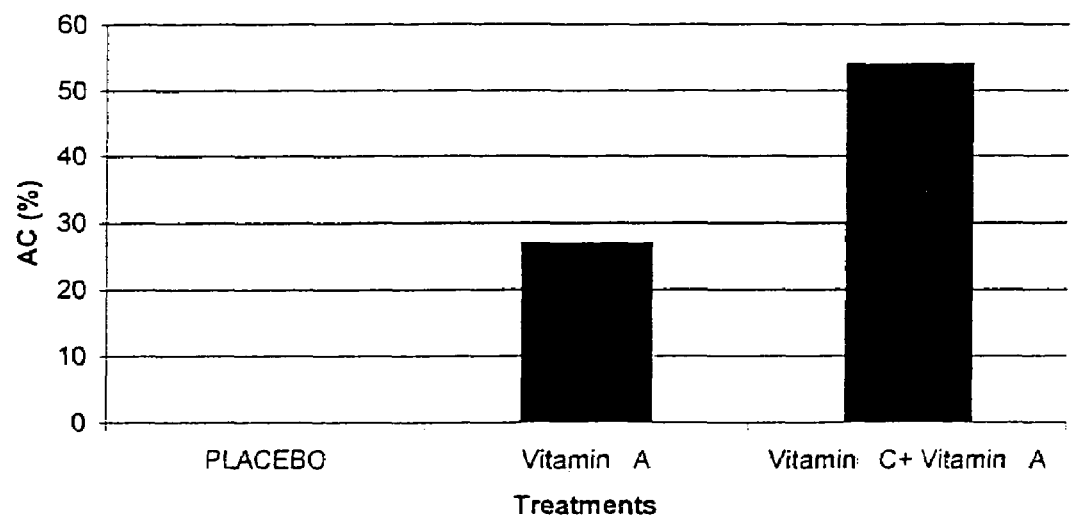
FIG. 2 - With exposure to radiation
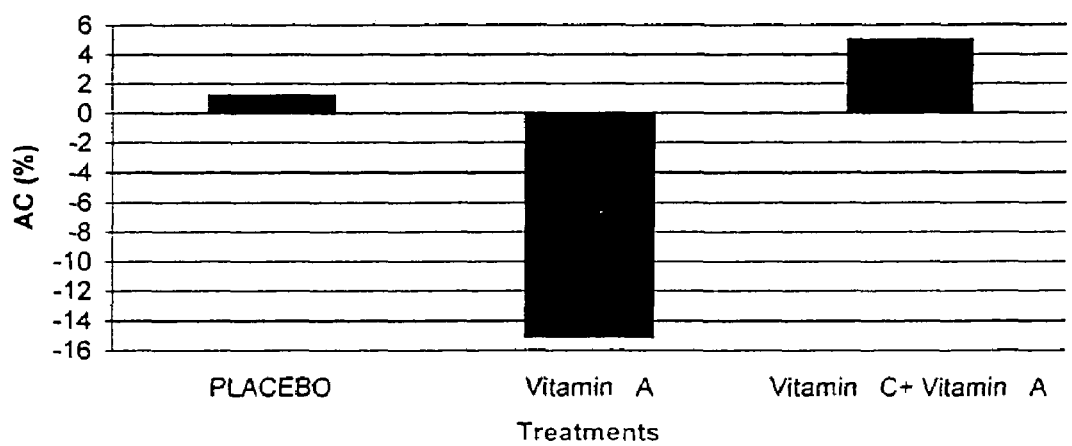

PROCESS AND COMPOSITION FOR ENHANCING THE ACTION OF VITAMIN A ON THE CELLULAR ACTIVITY OF AN INDIVIDUAL, AND USE OF VITAMIN C

FIELD OF THE INVENTION

The present invention refers to a process for improving the effects of Vitamin A used in cosmetic compositions in order to enhance the cellular activity of an individual.

BACKGROUND OF THE INVENTION

The compound generically known as Vitamin A comprises retinol and its derivatives, also known as retinoids, in addition to its acidic or aldehyde form, respectively retinoic acid and retinal. Retinoic acid has application in the pharmaceutical and cosmetic industries being, however, prohibited in several countries for cosmetic use due to the adverse effects of irritability which it may cause. Examples of pharmaceutical applications of retinoic acid can be found in the article "Relationships between structure and activity of retinoids", published by Nature, Volume 236, pages 110–113, of Sep. 9, 1996.

In the cosmetic area Vitamin A is usually employed in the form of retinol or some of its retinoids such as retinyl palmitate, and the use of retinol causes various biologic activities, many of which are highly desirable in cosmetic compositions, particularly in those intended to improve the general conditions of the skin of the individual subjected to the topic use thereof. Results achieved by the topic use of Vitamin A are described in passages contained in pages 82–119 of the article entitled "Vitamin A Complex", written by Wade Cheng, PhD and Shirley DePetris and published by Skin Inc., March/April 1998.

Moreover, regulation and balance of the epidermal cellular growth through the total synthesis of collagen, among others, such as retention of water in the skin, are also known as effects resulting from the use of Vitamin A in its pure form, called Retinol.

One problem resulting from the use of Vitamin A, either in its pure form or as a derivative, is that, on the one side it promotes the effects of increasing the cellular activity at the level of the dermis and epidermis, accelerating the process of proliferation and differentiation of the keratinocytes and reorganization of the fibers of the dermis (collagen and elastin). But on the other side it must be administered at low doses due to its toxicity. This fact limits the use of Vitamin A and its derivatives to lower contents or requires the utilization of other means that are able to minimize the discomfort of irritation in the skin.

In fact, the use of retinol at low contents is quite common, as shown by several studies, such as the one conducted by the Hamburg Clinic of Experimental Dermatology, in Germany, which doscloses tests with low contents of Retinol (0.034%) for men and women with age between 22 and 34 years and which show that such a concentration of retinol could reduce the amount and the deepness of wrinkles. Therefore, this study generically shows the effect of reducing wrinkles by the use of low contents of retinol.

On the other hand, what has been observed is that, even though low concentrations of retinol effectively cause little or no irritation, the results on the skin can remain below the desired levels for the present standards of demand of the consumers in view of the small amount of retinol incorporated in the cosmetic composition and available for its biological action.

In this respect, there have been attempts to obtain compositions of Vitamin A that present effective action and do not cause adverse effects, for instance, the irritation of the skin. As an example, documents U.S. Pat. No. 5,516,793 and U.S. Pat. No. 5,703,122 in the name of Avon Products, Inc., are incorporated herein as prior art references. These documents describe a generic association of amounts ranging from 0.5 to 25% by weight of Vitamin C with several irritating active principles, among which Vitamin A is included. This association, however, has the exclusive purpose of reducing irritation of the skin caused by Vitamin A.

It is therefore an objective of the present invention to provide an alternative for the use of Vitamin A at such concentrations that enable an increase in its properties which are beneficial to the skin, without presenting the problems cited above.

SUMMARY OF THE INVENTION

The present invention refers to a process for enhancing the action of Vitamin A on the cellular activity of an individual comprising the association of Vitamin C with Vitamin A, which will be applied to the referred-to individual at a weight ratio ranging from about 1:1 to about 10:1.

In another aspect, the invention refers to a composition for enhancing the action of Vitamin A on the cellular activity of an individual comprising Vitamin C in association with Vitamin A at a weight ratio in the range from about 1:1 to 10:1.

The invention further refers to the use of Vitamin C for enhancing the action of Vitamin A on the cellular activity of an individual.

BRIEF DESCRIPTION OF THE DRAWINGS

FIG. 1 shows a graph representing the increase obtained in the cellular activity of a reconstituted skin by the synergistic effect of an association of Vitamin C with Vitamin A according to the invention as compared to the cellular activity of a reconstituted skin treated only with pure Vitamin A.

FIG. 2 shows the synergistic effect on the recuperation and the increase in the cellular activity in reconstituted skin treated with Vitamin A associated with Vitamin C when subjected to ultraviolet irradiation.

DETAILED DESCRIPTION OF THE INVENTION

After detailed studies the inventors have found that the association of Vitamin C added to compositions containing Vitamin A at a weight ratio ranging from about 1:1 to about 10:1, preferably from about 1:1 to about 5:1, and more preferably from about 1:1 to about 2:1, provides a surprising increase in the cellular activity effects of Vitamin A on an individual.

"Vitamin C" useful for the present invention comprises Vitamin C in its pure form or its derivatives, namely L-ascorbic acid in its molecular form as well as its salts and esters such as ascorbyl phosphate.

As used herein, the expression "an increase in the cellular activity" means the occurrence of a benefit brought about by the increase or improvement at least in one of the situations selected from the maintenance of the cellular condition, the cellular proliferation and the metabolic activity especially in cutaneous cells.

Tests carried out on reconstituted skin show that a treatment of the skin in vitro with the association of Vitamin C with Vitamin A according to the present invention promotes an unexpected synergistic increase in the cellular activity of 100% as compared to the cellular activity observed in the same skin treated exclusively with pure Vitamin A or retinol (FIG. 1).

In the same surprising way, it has been noted that the association of Vitamin C with Vitamin A promotes reconstitution, recuperation and increase in the cellular activity of the skin, even when the individual is subjected to ultraviolet irradiation, which is recognized to cause deleterious effects on the skin and its cells. Tests carried out to this respect show a synergistic effect of reconstitution and increase in the cellular activity of 5% on reconstituted skin treated with Vitamin A associated with Vitamin C when subjected to ultraviolet irradiation (FIG. 2).

The association of Vitamin C with Vitamin A according to the present invention may be carried out at the moment of the application of these compounds to the individual, but it can also be advantageously formulated as a cosmetic composition containing the two vitamins at a weight ratio ranging from about 1:1 to about 10:1, preferably from about 1:1 to about 5:1, and more preferably from about 1:1 to about 2:1 of Vitamin C to Vitamin A.

According to a preferred embodiment of the invention, said cosmetic composition comprises, by weight, about 0.01 to about 0.9% of Vitamin C and from about 0.008 to about 0.20% of Vitamin A, based on the total weight of the composition. Even more preferably, the composition contains from about 0.02 to about 0.8% by weight of Vitamin C and from about 0.009 to about 0.16% by weight, of Vitamin A and even more preferably the composition contains 0.02 wt. % of Vitamin C and from about 0.009 to about 0.02 wt % Vitamin A, all the percentages based on the total weight of the composition.

It is noted that, even at very low concentrations, Vitamin A associated with Vitamin C as defined in the present invention achieves the desired effects of increase in the cellular activity.

The cosmetic compositions containing Vitamin A and Vitamin C at the proportions cited above can also contain other appropriate additives and formulation aids, such as antioxidants for combating free radicals. Among the useful antioxidants, Vitamin E stands out, both in its pure form presented by di-α-tocopherol, and as its derivatives such as dil-α-tocopherol, or 2,6-di-terc-buthyl-p-cresol (BHT).

The introduction of Vitamins C, A and t in microspheres increases their action and makes it possible for them to reach the deeper layers of the skin with greater, or even total, integrity, without degeneration of the product in the path between the application area end the place of action.

In a particularly preferred way, the cosmetic compostions according to the present invention are formulated in such a manner, that their components are contained in organic vectors such as microspheres and, more particularly, in microspheres or microcapsules containing biologically active material ("Talasferas") such as those defined In U.S. Pat. No. 5,395,620, or in Brazilian patent application PI 9706994-7, filed in the name of this same applicant.

The composition as described above may contain a plurality of said microspheres, in a dispersed form, comprising Vitamin A and, for example, an antioxidant such as Vitamin E, inserted into a first group of microspheres, and Vitamin C inserted into a second group of microspheres. A particularly preferred composition comprises a first group of microspheres containing Vitamin A at an average concentration of 0.014% and Vitamin E at an average concentration of 0.0005% by weight, and a second group of microspheres containing 0.02% by weight of Vitamin C.

Advantageously, in association to the groups of microspheres previously mention, such a composition may further contain, in addition to Vitamin A and Vitamin E, and cosmetic compounds selected from the group consisting of skin structures, preferably squalan and sphingolipide complexes, micronutrients of the skin, preferably seaweed extract, sensorial agents, for example, moisteners such as glycerin and hydroxy prolisilane C, emollients such as butylene glycol and cetyl lactate and silicones such as cyclomethicone, solar protection factors such as Parsol 1789 (Butyl methoxydibenzoyl methane) and Eusolex 6300 (3-(4-methylbenzylidene) Camphor), emulsifiers, preferably Carbopol 1342 (acrylates/C10–30 alkyl acrylate crosspolymer) associated to trietanolamin and soybean lecitin, thickeners, preferably xanthan gum; sequestrants, preferably EDTA, antioxidants such as BHT and dl-α-tocopherol, fragrances, conservants, water and mixtures thereof.

In one particular embodiment of the present invention, the composition containing Vitamin A and Vitamin C may be in the form of an emulsion and, in this case, the Vitamin C preferably used is L-ascorbic acid stabilized by hydrogen-bridge-forming compounds. Such processes of stabilizing L-ascorbic acid are described in applications PI 9704418-0 and PI 9704728-7, also filed by this same applicant.

As an illustrative example of another possible embodiment of the present invention the composition is formulated as a gel in which the weight ratio of Vitamin C to Vitamin A is advantageously about 5:1, Vitamin C being present preferably in amounts of about 0.75% and Vitamin C being present in amounts of about 0.16 wt %, based on the total weight of the composition. This gel composition may further contain thickeners such ascarbopol, fragrances, conservants and water.

What is claimed is:

1. A composition for enhancing the action of Vitamin A on the cellular activity of an individual, comprising a plurality of dispersed microspheres, said plurality of microspheres comprising Vitamin A and an antioxidant inserted into a first group of microspheres, and Vitamin C inserted into a second group of microspheres;

wherein said microspheres are made of biologically active material; and wherein the composition comprises an emollient selected from the group consisting of butylene glycol, cetyl lactate, and combinations thereof.

2. The composition according to claim 1, wherein Vitamin C is present at a concentration of about 0.02% by weight, and Vitamin A is present at a concentration of about 0.009% to 0.02% by weight, based on the total weight of the composition.

3. The composition according to claim 2, wherein Vitamin C is contained in the second group of microspheres at a concentration of 0.02%.

4. The composition according to claim 3, wherein the first group of microspheres contains Vitamin A at an average concentration of about 0.014% by weight, based on the total weight of the composition.

5. The composition according to claim 4, wherein the first group of microspheres contains Vitamin A at an average concentration of 0.014% and Vitamin E at an average concentration of 0.0005% by weight, and further contains cosmetic compounds selected from the group consisting of skin structures, micronutrients of the skin, sensory agents, solar protection factors, emulsifiers, thickeners, sequestrants, antioxidants, fragrances, conservants, water and mixtures thereof, wherein said skin structures are squalan and sphingolipide complexes, said micronutrients of the skin is seaweed extract, and said sensory agents are selected from the group consisting of moisteners, and silicones.

6. The composition according to claim 1, wherein the Vitamin C to Vitamin A weight ratio ranges from about 1:1 to about 10:1.

7. The composition according to claim 1, wherein the antioxidant is Vitamin E.

8. The composition according to claim 5, wherein the moisteners are selected from the group consisting of glycerin, hydroxy prolisilane C, and combinations thereof.

9. The composition according to claim 5, wherein the silicone is cyclomethicone.

10. The composition according to claim 5, wherein the solar protection factors are selected from the group consisting of butyl methoxydibenzoyl methane, 3-(4-methylbenzylidene) camphor, and combinations thereof.

11. The composition according to claim 5, wherein the emulsifiers are selected from the group consisting of acrylates/C10–30 alkyl acrylate crosspolymer associated with trietanolamin, soybean lecitin, and combinations thereof.

12. The composition according to claim 5, wherein the thickener is xanthan gum.

13. The composition according to claim 5, wherein the sequestrant is ethylene diamine tetraacetate (EDTA).

14. The composition according to claim 5, wherein the antioxidants are selected from the group consisting of buthyl hydroxytoluene (BHT), dl-α-tocopherol, and combinations thereof.

15. A composition for enhancing the action of Vitamin A on the cellular activity of an individual, comprising a plurality of dispersed microspheres, said plurality of microspheres comprising Vitamin A and an antioxidant inserted into a first group of microspheres, and Vitamin C inserted into a second group of microspheres; wherein said microspheres are made of biologically active material, wherein the Vitamin C is present in an amount effective for enhancing the action of the Vitamin A on the cellular activity of an individual; and wherein the composition comprises an emollient selected from the group consisting of butylene glycol, cetyl lactate, and combinations thereof.

16. A composition for enhancing the action of Vitamin A on the cellular activity of an individual, comprising a plurality of dispersed microspheres, said plurality of microspheres comprising Vitamin A and an antioxidant inserted into a first group of microspheres, and Vitamin C inserted into a second group of microspheres;

wherein said microspheres are made of biologically active material, and Vitamin C is present at a concentration of about 0.02% by weight, and Vitamin A is present at a concentration of about 0.009% to 0.02% by weight, based on the total weight of the composition; and wherein the composition comprises an emollient selected from the group consisting of butylene glycol cetyl lactate, and combinations thereof.

* * * * *